United States Patent [19]

Bernard

[11] Patent Number: 5,084,027

[45] Date of Patent: Jan. 28, 1992

[54] NEEDLE COVER WITH SAFETY DISPOSAL CHAMBER

[76] Inventor: Daniel H. Bernard, 3 Bradshaw Dr., Ossining, N.Y. 10562

[21] Appl. No.: 733,103

[22] Filed: Jul. 19, 1991

[51] Int. Cl.[5] .............................. A61M 5/32
[52] U.S. Cl. ..................... 604/192; 604/263
[58] Field of Search ............... 604/198, 199, 192, 110, 604/187, 263

[56] References Cited

U.S. PATENT DOCUMENTS

| | | | |
|---|---|---|---|
| 4,728,321 | 3/1988 | Chen | 604/110 |
| 4,950,242 | 8/1990 | Alvarez | 604/192 |

*Primary Examiner*—John D. Yasko
*Attorney, Agent, or Firm*—Martin J. Spellman, Jr.

[57] ABSTRACT

A dual chamber cover for hyperdermic needles to assure that they may not be reused and to prevent accidental pricking with a used needle. The first chamber serves to cover the needle initially prior to use. The second chamber which is inversely joined along its cylindrical walls to the first chamber has three reservoirs which contain respectively, a first component of a two component resin, a second component of the resin, and fiber filler. The reservoirs are separated by frangible disks. The second chamber is closed at one end and initially closed at the other end by a needle penetrable rubber disk. After a needle has been used, it is inserted through the rubber disk, through the first chamber and the first resin component, the first frangible disk, the second reservoir chamber and second resin component, the second frangible disk, and on into the third reservoir, mixing the resin components and fiber filler together which harden around the needle end to permanently prevent its reuse and accidental pricking.

1 Claim, 2 Drawing Sheets

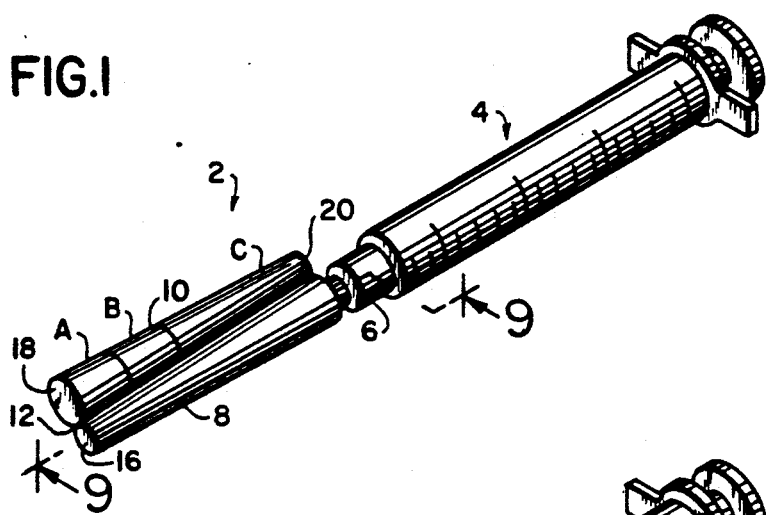
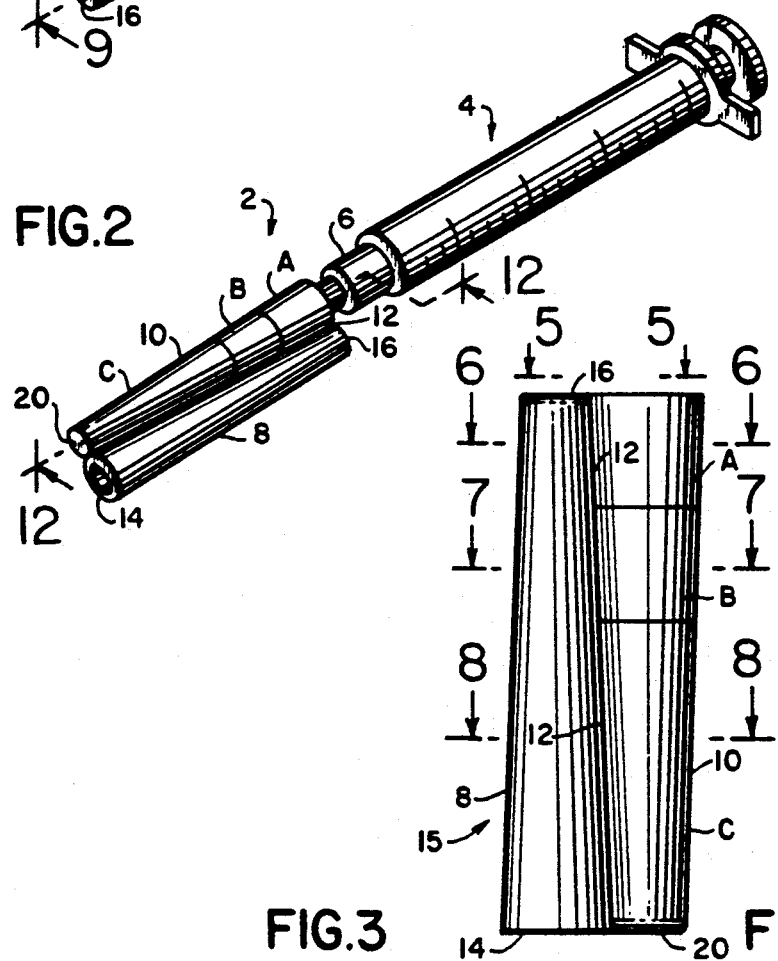

NEEDLE COVER WITH SAFETY DISPOSAL CHAMBER

BACKGROUND OF THE INVENTION

1. Field of the Invention

The present invention is concerned with providing a safe means for preventing hypodermic needles from being reused for illegal and unsanitary purposes as well as the safety of an individual who would come in contact with a discarded syringe.

At present, needle syringes come with a removable plastic or rubber cap over the end of the needle which prevents inadvertent pricking and assures cleanliness prior to use. It is routine practice for those using a syringe legitimately to replace the cover after use and prior to discarding it in order to avoid inadvertent pricking. As is well know, discarded needles are often obtained for illegal drug usage or are washed up on beaches with other refuse. These needles present a hazard to those using the beaches.

Of particular concern presently, is usage of syringes in drawing blood for evacuated blood collection tubes using hypodermic needles and how to prevent the reuse of the needle.

The present device provides a dual chamber cover for such needles. One chamber is generally similar to present plastic covers, and the second chamber in which the needle is placed after use contains a two component plastic resin and preferably a filler. When the used needle is inserted in the second chamber, the two resin components are mixed together and in preferred embodiments with the filler which causes the needle to be permanently encapsulated within the second chamber with the resin filling the end of the needle and the needle cast in the hardened resin and filler making it impossible to reuse the needle or be pricked by it.

2. Prior Art

U.S. Pat. No. 4,950,242—ALVAREZ discloses a cover for a hypodermic needle-syringe which has a longitudinal partition dividing the cover into a first chamber and a second chamber. One of the chambers is for conventional storage of the needle before use, whereas the second chamber has a longitudinal extending slot in the side wall for placing the used needle in the second chamber laterally to minimize the risk of a finger prick by trying to place the needle into the open end axially. The inner end of the second chamber is also provided with a needle-disabling, clogging or occluding material such as a soft rubber or plastic-like substance which is penetrated by the needle so as to lodge into the lumen of the needle thereby preventing the needle from being used for injection.

U.S. Pat. No. 4,728,321—CHEN reference shows a syringe cap that has a hollow cap body at the end comprising an adhesive holding plug mounted slideably on the cap body and moveable between an extended and a closed position. Then the plug is moved towards the needle it becomes permanently cemented to the used needle by means of an adhesive held in the plug when the needle pierces the closed end of the plug.

The following patents are of background interest to illustrate various other efforts of prior technology attempting to make the usage o disposal of syringes needles safer.

U.S. Pat. No. 4,643,772—SMITH, J. utilizes a cap with a longitudinal side opening to prevent finger pricking when recovering the needle.

U.S. Pat. No. 4,728,320—CHEN discloses a syringe cap that has a slideable hammer body at the end which, when struck, serves to deform the needle and engage the end of the cap.

U.S. Pat. No. 4,804,372—LAICO ET AL discloses an injection needle sheath which, after injection, is automatically activated to enclose the needle end.

U.S. Pat. No. 4,976,699—GOLD discloses a syringe cover which is hinged at the base to uncover and recover the needle by hinged lateral movement and has a locking mechanism permanently securing the needle after use. The specification of this patent also includes an extensive list of patents and publications in this area.

U.S. Pat. No. 4,985,020—KASUYA discloses a needle cap having a guide and tab handle for the cap to eliminate the danger of finger pricking.

None of the foregoing patents discloses or suggests the needle trap device of the present invention which safely and conveniently traps and permanently encapsulates the end of a used syringe needle within a hardened two component resin carried in a chamber.

SUMMARY OF THE INVENTION

The present invention provides a convenient means to use two chamber needle cover or trap for covering hypodermic needles prior to use and most importantly for safely disposing of the needle after use.

The cover comprises a first cylindrical chamber constructed like generally known needle covers which cover the needle prior to use. The walls of the open base of which frictionally engage the needle base prior to use.

A second cylindrical chamber is secured to or integral with the first chamber and the longitudinal axii of the two chambers are substantially parallel to each other. The closed end of the second chamber lies opposite the open end of the first chamber and vise-versa.

The open end of the second chamber is temporarily sealed at the open end thereof with a needle penetrable self-sealing rubber disk or gasket. Placed inwardly from the gasket is a needle frangible first disk defining a closed reservoir A between the rubber disk, walls of the chamber and the first frangible disk; longitudinally spaced from the first frangible disk is a second frangible disk defining a reservoir B within the walls of the chamber, and the two frangible disks, and the second frangible disk, walls and closed end of the chamber define a reservoir C.

Reservoirs A and B respectively each contain one different part of a two component resin which rapidly hardens when the components are mixed. Reservoir C contains a fiber filler such as cotton.

After the needle is used, it is safely disposed by placing the needle in the second chamber, passing through the sealing disk and one component, breaking the first tangible disk thereby mixing the two resin components, and breaking the second frangible disk to mix the hardening resin mixture with the filler. The needle is permanently embedded in the resin and filler which is formulated to harden within moments, thereby safely encapsulating the needle in the second closed end chamber rendering it incapable of reuse and preventing it pricking anyone.

BRIEF DESCRIPTION OF THE DRAWING

In the accompanying drawing which forms a part of the specification:

FIG. 1 is a view of the needle cover on a needle syringe prior to use of the needle;

FIG. 2 is a similar perspective view of the needle cover and syringe after use, with the needle embedded in the disposable chamber portion of the cover;

FIG. 3 is a plan view of the cover;

FIG. 4 is a side view of the cover, partially in section;

ILLUSTRATIVE SPECIFIC EMBODIMENT

Figure 5:
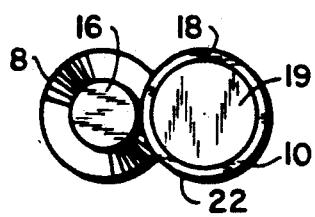
FIG. 5 is a top view of the cover in FIG. 3.
Figure 6:
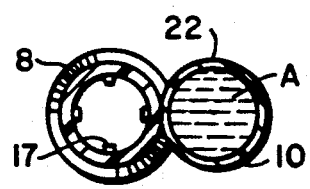
FIG. 6 is a section view along lines 6—6 of FIG. 3.
Figure 7:
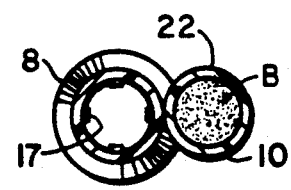
FIG. 7 is a section view along lines 7—7 of FIG. 3.
Figure 8:
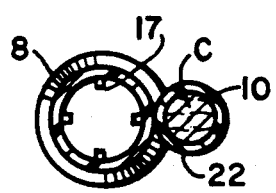
FIG. 8 is a section view along lines 8—8 of FIG. 3.
Figure 9:
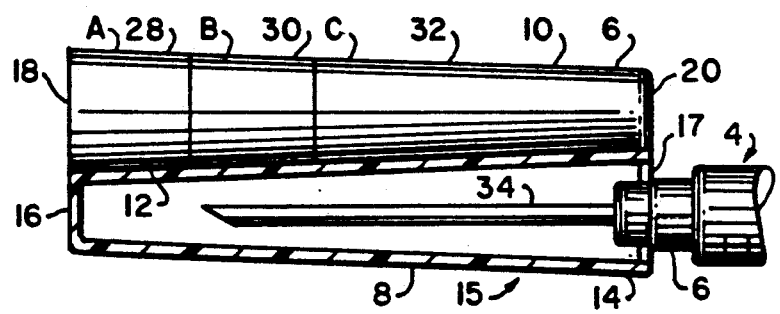
FIG. 9 is a plan view partially in section and cut away of the cover showing the needle syringe covered before use.
Figure 10:
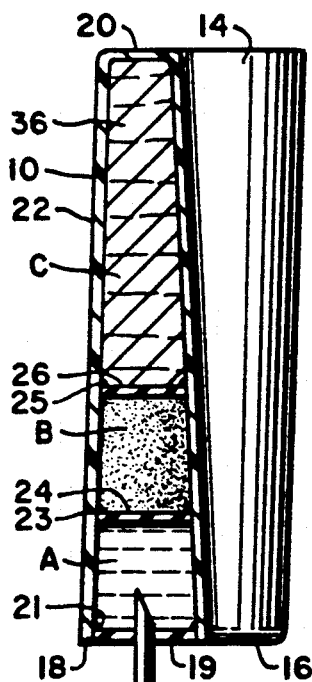
FIG. 10 is a plan view partially in section showing the needle initially entering the disposal chamber after use.
Figure 11:
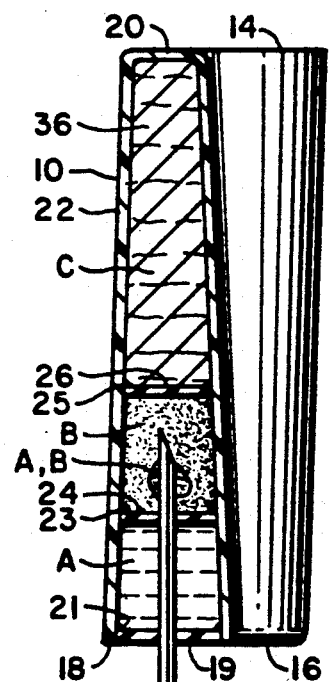
FIG. 11 is a similar view to that of FIG. 10 showing the needle further penetrating section B.
Figure 12:
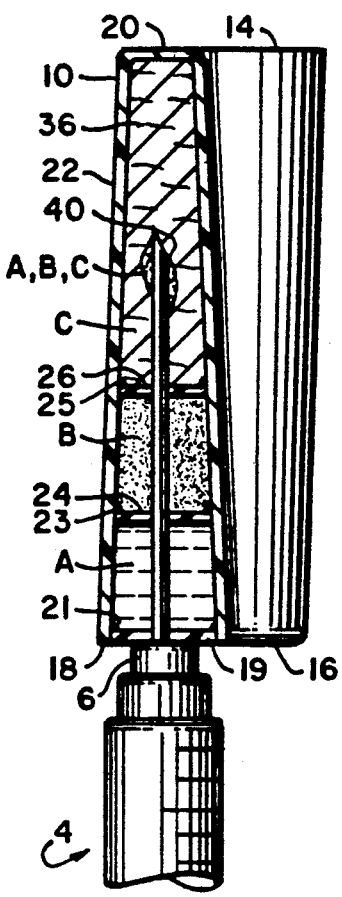
FIG. 12 is a similar view to that of FIG. 11 showing the needle all the way into the disposal chamber having further penetrated section C.

Referring to FIGS. 1 and 2 of the drawing, the cover 2 of the present invention is shown on the needle syringe 4 having a needle base 6 of conventional structure prior to use.

The cover 2 comprises a first hollow truncated cone or chamber 8 made of plastic material having an open base end 14, a closed distal end 16, and walls 15 the inside of which at their base 14 project inwardly at 17 frictionally engage the base 6 of the needle 34 on the syringe 4.

The cover 2 also comprises a second hollow plastic truncated cone or generally cylindrical chamber 10 joined to the chamber 8 along merge line 12. Preferably chambers 8 and 10 are molded integrally but they may be constructed separately and later joined by an adhesive or other means. In the example, they are integrally molded together.

The chamber 10 has a temporarily closed base end 18 with a needle penetrable self sealing rubber disk 19, walls 22, and a closed end 20.

The disk 19 in the embodiment shown is a rubber disk secured by adhesive to the internal end surface of the wall 22 at the base 18 thereof. The disk 19 may be supported by nibs 21 molded to the walls 22. Spaced inwardly from disk 19 and apart therefrom and from each other are needle penetrable and frangible disks 24 and 26. They are very thin plastic metal disks or alternatively metal foil may be used. They are supported by nibs 23 and 25 and are press fitted or adhesively secured to the walls 22. The walls 22 of the chamber 10 and disks 19 and 24 define a storage reservoir section A; disks 24 and 26, and walls 22 define a storage reservoir section B; and disk 26, walls 22 and end 20 define a reservoir section C.

Prior to use, disks 19, 24 and 26 maintain reservoirs A or 28, B or 30 and C or 32 separated, isolated from each other and the outside environment.

Reservoir C contains a filler fiber such as cotton indicated at 36. Reservoir B, one part of a two component resin and reservoir A the second part of a two component resin such as epoxy. The disk 24 and 26 are of a frangible material such as thin plastic or metal foil which as the end 40 of a needle 34 strikes them they shatter or tear open allowing the first and second parts of the resin to blend together and mix with the filler causing the needle to be filled with resin and encased within the now resin impregnated fiber 38 at the small end of the chamber 10. The needle 34 is permanently clogged and closed at the end 40 preventing its future use and embedded in the fiber filled and mixed resin of components A and B which cures rapidly to a hard substantially inert solid encased within chamber 10.

The resin system used in the illustrative embodiment comprises a diglycidyl ether of bisphenol A sold as Epon 828 as component A and triethylenetetramine (TETA) as component B. Other two component resins may be utilized.

Thus, the user will first uncover the needle by removing the cover 2 with the chamber 8 covering the needle 34, utilizing the syringe 4 for drawing blood or other use, and when finished, place the needle 34 with its point 40 penetrating through disk 18 into component A, breaking disk 24 to mix components A & B and then breaking disk 26 to carry the Mixing resin components into the filler section C. The filler and resin surround the needle 34 harden within less than a minute and encase the needle 34 permanently in the chamber.

While the invention has been described by reference to an illustrative embodiment, it is not intended that the novel device be limited thereby, but that modifications thereof are intended to be included as falling within the broad spirit and scope of the foregoing disclosure, the following claims and the appended drawings.

What is claimed is:

1. A needle cover for use with hyperdermic syringes comprising a first chamber closed at one end and open at its second end, walls adjacent said second end of said chamber dimensioned and adapted to removeably and frictionally engage a needle base of said syringes; a second chamber closed at one end and initially closed at a second and wider end by a self-sealing needle penetrable rubber disk, a first reservoir defined by annular walls of said second chamber and said penetrable rubber disk and a first frangible disk spaced from said penetrable rubber disk; a second reservoir defined by said annular walls, said first frangible disk and a second frangible disk, spaced from said first frangible disk; and a third reservoir defined by said annular walls, said closed end and said second frangible disk, said first reservoir containing one component of a two component resin, said second reservoir containing a second component of said resin system, and said third reservoir containing fiber filler for said resin, said first and second chambers being joined inversely along their walls and with their longitudinal axii substantially parallel.

* * * * *